(12) United States Patent
Lee et al.

(10) Patent No.: US 9,429,552 B2
(45) Date of Patent: Aug. 30, 2016

(54) APPARATUS AND METHOD OF PREPARING REFERENCE SOLUTION

(71) Applicant: KOREA INSTITUTE OF GEOSCIENCE AND MINERAL RESOURCES, Daejeon (KR)

(72) Inventors: Kilyong Lee, Daejeon (KR); Yoonyoel Yoon, Daejeon (KR); Sooyoung Cho, Daejeon (KR)

(73) Assignee: KOREA INSTITUTE OF GEOSCIENCE AND MINERAL RESOURCES, Daejeon (KR)

( * ) Notice: Subject to any disclaimer, the term of this patent is extended or adjusted under 35 U.S.C. 154(b) by 364 days.

(21) Appl. No.: 14/095,598

(22) Filed: Dec. 3, 2013

(65) Prior Publication Data
US 2015/0068276 A1   Mar. 12, 2015

(30) Foreign Application Priority Data

Sep. 6, 2013   (KR) .......................... 10-2013-0107470

(51) Int. Cl.
*G01N 33/00* (2006.01)
*G01N 1/38* (2006.01)
(Continued)

(52) U.S. Cl.
CPC ............ *G01N 33/0006* (2013.01); *G01N 1/38* (2013.01); *G01N 15/088* (2013.01); *G01N 33/0011* (2013.01); *G01N 2001/2893* (2013.01); *G01N 2001/387* (2013.01)

(58) Field of Classification Search
CPC ........... G01N 33/0011; G01N 15/088; G01N 33/0006; G01N 1/38
USPC ......................................................... 73/23.2
See application file for complete search history.

(56) References Cited

U.S. PATENT DOCUMENTS

| 4,912,323 A | 3/1990 | Bhat et al. |
| 2005/0061737 A1* | 3/2005 | Linden .................. A01K 63/04 210/602 |
| 2015/0068285 A1* | 3/2015 | Lee ...................... G01N 15/088 73/38 |

FOREIGN PATENT DOCUMENTS

| KR | 1019990024427 | 4/1999 |
| KR | 100717953 | 5/2007 |

(Continued)

OTHER PUBLICATIONS

Lee, K. Y., et al., Determination of air-loop volume and radon partition coefficient for measuring radon in water sample, Journal of Radioanalytical and Nuclear Chemistry, May 21, 2013.

(Continued)

*Primary Examiner* — John Fitzgerald
*Assistant Examiner* — David Z Huang
(74) *Attorney, Agent, or Firm* — IP & T Group LLP

(57) ABSTRACT

The present invention relates to an apparatus and method of preparing a reference solution of a gaseous substance necessary for calibration of various measuring instruments used in measurement of the gaseous substance, such as radon (Rn-220) or a volatile substance, contained in seawater, subsurface water, surface water or the like. An apparatus of preparing a reference solution according to the present invention includes a gas component detector having two ports and configured to measure a concentration of a predetermined gaseous substance; a gas vessel having two ports and configured to accommodate the predetermined gaseous substance; a reference solution preparation vessel having two ports and configured to accommodate a predetermined liquid substance; pipe lines connecting the ports of the gas component detector, the gas vessel and the reference solution preparation vessel; and valves installed on the pipe lines.

19 Claims, 7 Drawing Sheets

(51) Int. Cl.
*G01N 15/08* (2006.01)
*G01N 1/28* (2006.01)

(56) References Cited

FOREIGN PATENT DOCUMENTS

| KR | 1020120094773 | 8/2012 |
| KR | 101237773 | 3/2013 |

OTHER PUBLICATIONS

Havelka, M., Radon-in-water standard, Applied Radiation and Isotopes, 2009, pp. 860-862, vol. 67.
Office Action issued by the Japanese Patent Office on Jan. 6, 2015.
Notice of Allowance issued by the Korean Intellectual Property Office on Jan. 14, 2015.

* cited by examiner

APPARATUS AND METHOD OF PREPARING REFERENCE SOLUTION

CROSS-REFERENCE TO RELATED APPLICATIONS

The present application claims priority from Korean Patent Application No. 10-2013-0107470, filed on Sep. 6, 2013, which is incorporated herein by reference in its entirety.

BACKGROUND OF THE INVENTION

1. Field of Invention

The present invention relates to an apparatus and method of preparing a reference solution, and more particularly, to an apparatus and method of preparing a reference solution of a gaseous substance necessary for calibration of various measuring instruments used in measurement of the gaseous substance, such as radon (Rn-220) or a volatile substance, contained in seawater, subsurface water, surface water or the like.

2. Description of the Prior Art

Radon is generated from three types of naturally occurring radioactive series, uranium series (U-238), actinium series (U-235), and thorium series (Th-232), and three isotopes of radon occur in nature: Rn-222 (having a half-life of 3.82 days), Rn-219 (having a half-life of 3.96 seconds) and Rn-220 (having a half-life of 55.6 seconds). Among the three radon isotopes, Rn-222 having the longest half-life of 3.82 days is commonly referred to as radon.

Radon is a colorless and odorless inert gas such as helium (He) or neon (Ne) and is known as a very harmful substance to the human body when it is inhaled. International Agency for Research on Cancer (IARC) classifies radon along with asbestos as class one carcinogens, and Environment Protection Agency (EPA) classifies radon as a carcinogen after smoking.

In practice, a risk of radon is mostly caused by radon progenies rather than radon itself. Although there are eight types of radon progenies, when considering a generation rate and half-life, a representative nuclide dangerous to the human body includes Po-218, Po-214, Bi-214, Pb-214 and the like (National Council on Radiation Protection and Measurements, NCRP, 1988). All the radon progenies are heavy metals, have chemicophysical properties completely different from radon, and easily adsorbed to air suspended substances such as aerosol and dust.

It has been known that after radon occurring in the air and radon progenies adsorbed to suspended substances are introduced along with other gaseous substance into the human body when they are inhaled and accumulated on a lung wall, lung cancer is caused by the transformation of lung cells exposed to alpha particles generated during the decay of the radon and the radon progenies.

It has been known that a mean effective radiation exposure of radon to an ordinary human body is higher than that of total natural radioactivity except radon or medical treatment activity such as X-ray examination and also much higher than that caused by industrial activity such as in a nuclear power plant. The EPA reports that 5,000 to 20,000 persons die of lung cancer due to radon each year in the United States based on the calculations of scientists.

It has also been known that the concentration of radon and radon progenies occurring in the air mainly depends on the uranium content of soil distributed in the vicinity of us and about 80% of radon in the air originates from the surface layer of soil. Also, radon has a higher solubility in water than other inert gas. Therefore, subsurface water serving as a carrier of radon released from rock or fissure, with which the subsurface water comes into contact in subsurface flow paths, contains 1,000 to 10,000 times more radon than seawater or surface water such as river water.

Radon is receiving attention as a harmful substance to the human body and also in various fields including health science, environmentology, oceanography, climatology, and the like due to physicochemically stable inert properties, a high radon content in subsurface water, and the like. Recently, as interests in conservation, securing and development of subsurface water are increased, radon is being used as a very suitable tracer in connection studies of subsurface water and surface water. In addition, radon tends to be actively used in analysis of generating factors and countermeasure research of algal blooms, red tides and the like due to the subsurface water outflow to the sea or lake.

As radon receives attention in a variety of fields as described above, a device and method of measuring radon has been constantly developed. Typical methods of measuring radon developed so far include gamma spectroscopy of measuring radon progenies, Pb-214 and Bi-214, a Lucas cell method using scintillation cells, a liquid scintillation counting (LSC) method using a liquid scintillation solution, and the like. In order to precisely measure radionuclides or chemical components, calibration of a device used in the measurement should be preceded. The calibration of such a device is generally performed using a reference or standard substance necessary thereto.

The calibration standard substance should secure homogeneity and long-term stability and need matrix matching. However, unfortunately, no commercialized radon reference solution has been developed so far since radon has a half-life of 3.82 days, which is not suitable for being used as a standard substance in terms of long-term stability and matrix matching.

Because of these problems, a reference solution of radium (Ra-226, a half-life of 1,600 years), which is a parent nuclide of radon, is commercialized as an alternate substance of radon reference solution. However, such a radium standard substance is prepared by synthesizing a radium compound through complicated procedures and dissolving it in strong acid. Therefore, when the radium standard substance is used after being diluted, the radium standard substance has different components dissolved therein from an actual target object desirous to be measured, such as subsurface water, seawater, river water, or leachate, which increases uncertainty of measurement, resulting in inaccurate calibration of a device. In order to accurately perform indoor air pollution evaluation of radon, effects evaluation of subsurface water-surface water using a radon tracer, and the like, it is urgent to develop a radon reference solution with matrix matching with a target object to be measured.

SUMMARY OF THE INVENTION

Accordingly, the present invention is conceived to solve the aforementioned problems in the prior art. An objective of the present invention is to provide an apparatus and method of simply preparing a reference solution of a predetermined gaseous substance, which can secure a matrix matching condition for calibration of a measuring device.

According to an aspect of the present invention for achieving the objectives, there is provided an apparatus of preparing a reference solution, including: a gas component detector having two ports and configured to measure a concentration of a predetermined gaseous substance; a gas vessel having two ports and configured to accommodate the predetermined gaseous substance; a reference solution preparation vessel having two ports and configured to accommodate a predetermined liquid substance; pipe lines connecting the ports of the gas component detector, the gas vessel and the reference solution preparation vessel; and valves installed on the pipe lines, wherein the pipe lines and the valves are arranged and installed to form a first loop wherein the gas component detector is not connected to both the gas vessel and the reference solution preparation vessel, a second loop wherein the gas component detector is connected to the gas vessel and not connected to the reference solution preparation vessel, and a third loop wherein the gas component detector is connected to the reference solution preparation vessel and not connected to the gas vessel, and the valves switches between the loops.

Preferably, the two ports of the gas component detector are respectively connected to the two ports of the gas vessel through two pipe lines, the valves are respectively installed on the two pipe lines, the valves are connected to each other through a pipe line, the valves are respectively connected to the two ports of the reference solution preparation vessel through two pipe lines, and each of the valves is a four-way valve.

Preferably, the gas component detector, the gas vessel, and the reference solution preparation vessel are serially connected to one another through pipe lines to form a single closed loop, the valves are respectively installed at the pipe lines in the vicinity of the two ports of the gas vessel and connected to each other through a pipe line, the valves are respectively installed at the pipe lines in the vicinity of the two ports of the reference solution preparation vessel and connected to each other through a pipe line, and each of the valves is a three-way valve.

The apparatus may further include a pump installed adjacent to the gas component detector.

The apparatus may further include a drying tube installed adjacent to the gas component detector.

Each port of the gas vessel may be provided with an opening/closing valve.

The reference solution preparation vessel may be configured to be removable from the apparatus and comprises a dual cap including a septum cap.

According to another aspect of the present invention, there is provided a method of preparing a reference solution, including: providing the above-described apparatus of preparing a reference solution; accommodating the predetermined gaseous substance and the predetermined liquid substance in the gas vessel and the reference solution preparation vessel, respectively; forming the second loop and maintaining it for a predetermined time; forming the first loop, maintaining it for a predetermined time, and measuring a concentration of the gaseous substance in the first loop by the gas component detector; forming the third loop, maintaining it for a predetermined time for the gaseous substance and the liquid substance to reach an equilibrium state in the reference solution preparation vessel, thereby obtaining a reference solution of the gaseous substance, and measuring a concentration of the gaseous substance in the third loop by the gas component detector; and calculating a gaseous substance concentration in the reference solution based on the respective gaseous substance concentrations in the first and third loops, respective internal volumes of these loops, a volume of the liquid substance, and a mass balance equation for the gaseous substance in these loops.

Before the second loop is formed, the method may further include additionally forming the first loop to measure a background concentration of the gaseous substance in the additional first loop by the gas component detector, wherein after forming the second loop, the gaseous substance concentrations measured in the first and third loops by the gas component detector are corrected by subtracting the background concentration therefrom.

A solid substance generating the gaseous substance may be accommodated in the gas vessel.

The gaseous substance may include radon or a volatile substance.

BRIEF DESCRIPTION OF THE DRAWINGS

The above and other objectives, features and advantages of the present invention will become apparent from the following description of a preferred embodiment given in conjunction with the accompanying drawings, in which.

DETAILED DESCRIPTION OF THE PREFERRED EMBODIMENT

Figure 1:
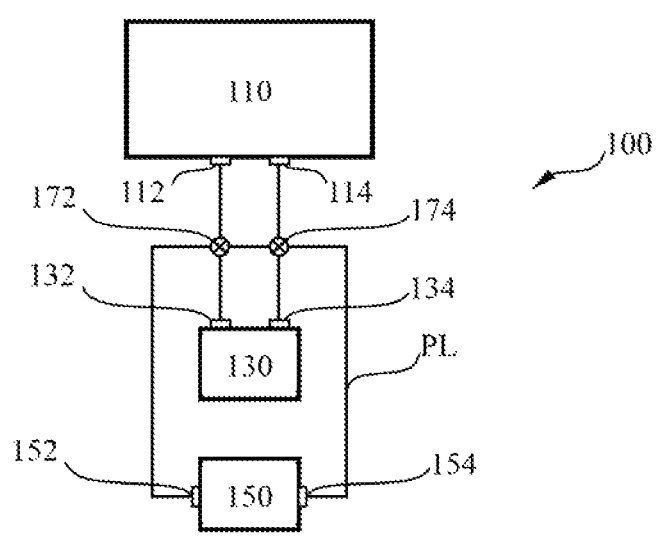
FIG. 1 is a schematic view of an apparatus of preparing a reference solution according to an embodiment of the present invention.

Hereinafter, preferred embodiments of the present invention will be described in detail with reference to the accompanying drawings. The following embodiments are provided only for illustrative purposes so that those skilled in the art can fully understand the spirit of the present invention. Therefore, the present invention is not limited to the following embodiments but may be implemented in other forms. In the drawings, the widths, lengths, thicknesses and the like of elements may be exaggerated for convenience of illustration. Like reference numerals indicate like elements throughout the specification and drawings.

Figure 2:
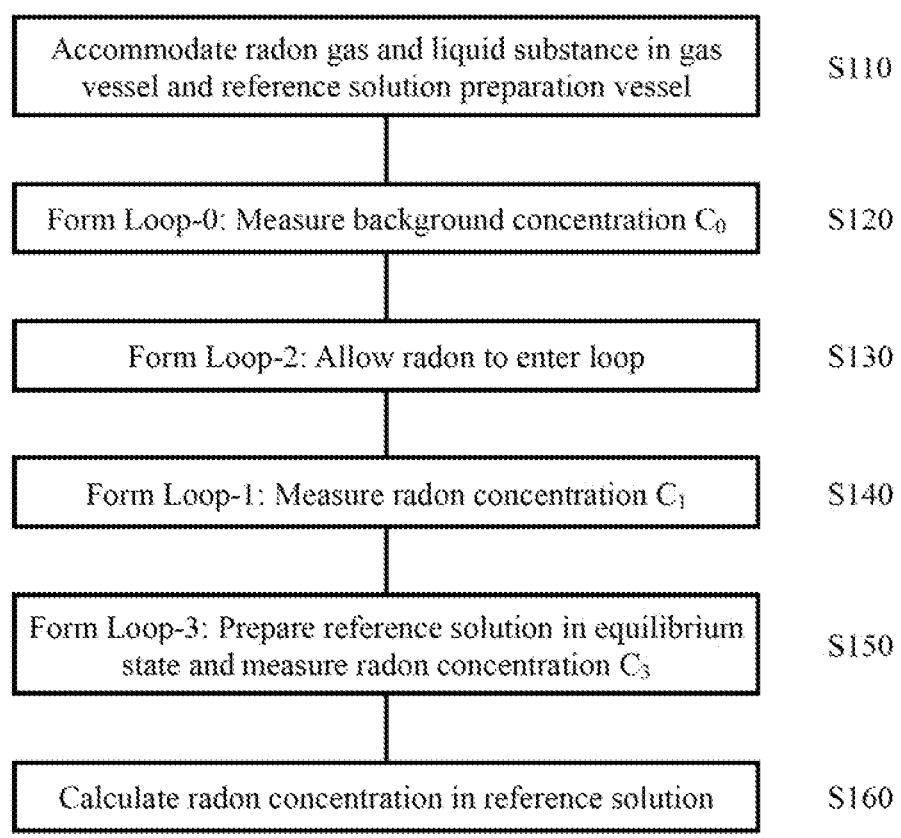
FIG. 2 is a flowchart illustrating a method of preparing a reference solution using the apparatus shown in FIG. 1.

FIG. 1 is a schematic view of an apparatus of preparing a reference solution according to an embodiment of the present invention; FIG. 2 is a flowchart illustrating a method of preparing a reference solution using the apparatus shown in FIG. 1; and FIGS. 3A to 3D are views showing loops formed in respective steps for preparing a reference solution using the apparatus shown in FIG. 1.

In the embodiment, an apparatus and method of preparing a radon reference solution will be described using radon as an example of a gaseous substance of a target object desirous to be measured. According to the present invention, a property of a gaseous substance dissolved in a liquid substance of the target object desirous to be measured is used, and thus, it is possible to apply the present invention to the preparation of a reference solution of other volatile substances as well as radon. That is, if a volatile substance is used as the gaseous substance of the target object desirous to be measured and the concentration of the used volatile substance can be measured, the present invention may be applied to the preparation of a reference solution of the volatile substance.

First, referring to FIG. 1, a radon reference solution preparation apparatus 100 according to an embodiment of the present invention includes a gas component detector 110 for measuring the concentration of radon gas, a gas vessel 130 for accommodating radon-enriched gas, a reference solution preparation vessel 150 for accommodating a liquid substance of a target object desirous to be measured, pipe lines PL for connecting the gas component detector 110, the gas vessel 130 and the reference solution preparation vessel 150 to one another, and a plurality of valves 172 and 174 installed at predetermined positions of the pipe lines PL to switch between a plurality of predetermined loops formed by the gas component detector 110, the gas vessel 130, the reference solution preparation vessel 150, and the pipe lines PL.

The gas component detector 110 is a pump built-in type and includes a component detection part for detecting the concentration of radon gas and input and out ports 112 and 114 respectively connected to pipe lines PL. Since the gas component detector 110 used in the embodiment has a pump installed therein, the pump operates to allow radon gas to flow into the gas component detector 110 through the pipe line PL connected to the input port 112 and to allow the radon gas to flow out through the output port 114 after the concentration of the radon gas is measured by the component detection part.

The gas vessel 130 and the reference solution preparation vessel 150 are airtight containers for accommodating radon gas and a liquid substance for preparing a reference solution, respectively. That is, when a radon reference solution, in which not only a pure substance such as distilled water or ethanol but also a mixture such as subsurface water, seawater, river water or leachate are used as a solvent, is prepared, a liquid substance of the target object desirous to be measured, such as distilled water, ethanol, subsurface water, seawater, river water, or leachate, is accommodated in the reference solution preparation vessel 150, and a radon enriched gas is accommodated in the gas vessel 130. Here, instead of the radon enriched gas, a solid substance generating radon gas may preferably be accommodated in the gas vessel 130. Here, the reference solution preparation vessel 150 should be partially filled with the liquid substance. The gas vessel 130 and the reference solution preparation vessel 150 are provided with two ports 132 and 134 and two ports 152 and 154, to which pipe lines PL are connected, respectively. The two ports 132 and 134 of the gas vessel 130 are preferably equipped with opening/closing valves, respectively.

Particularly, the liquid substance of the target object desirous to be measured is accommodated in the reference solution preparation vessel 150 and is then subjected to the steps described below, thereby resulting in becoming a radon reference solution in the reference solution preparation vessel 150. In order to use the prepared radon reference solution, the reference solution preparation vessel 150 may be provided with a cap for opening the vessel and be removable from the radon reference solution preparation apparatus 100 of the present invention.

After the radon reference solution is prepared, it is apprehended that the radon dissolved in the liquid substance accommodated in the reference solution preparation vessel 150 is volatilized in the air depending on temperature and pressure and leaks through a gap, for example, between the vessel and the cap. Therefore, when the prepared radon reference solution is used, the radon gas is released to the outside the moment the cap is opened, thereby changing the concentration of the radon in the reference solution. In order to prevent it, the reference solution preparation vessel 150 is preferably provided with a dual cap having an inner septum cap and an outer airtight cap.

In addition, after the radon reference solution is prepared, in order to remove the reference solution preparation vessel 150 from the reference solution preparation apparatus 100 of the present invention, it is preferred that the two ports 152 and 154 of the reference solution preparation vessel 150 be provided with opening/closing valves, respectively.

The input and output ports 112 and 114 of the gas component detector 110 are respectively connected to the two ports 132 and 134 of the gas vessel 130 through the two pipe lines PL. Here, the valves 172 and 174 are respectively installed in the middles of the two pipe lines PL, and the valves 172 and 174 are connected to each other through a pipe line PL. In addition, the valves 172 and 174 are connected to the two ports 152 and 154 of the reference solution preparation vessel 150 through the pipe lines PL. Here, each of the valves 172 and 174 installed in the pipe lines PL is a four-way valve.

By controlling the valves 172 and 174 in the state that the pipe lines PL and the valves 172 and 174 are connected and installed, predetermined loops Loop-0, Loop-1, Loop-2 and Loop-3 for measuring the radon concentration in the prepared radon reference solution may be formed.

Figure 3A:
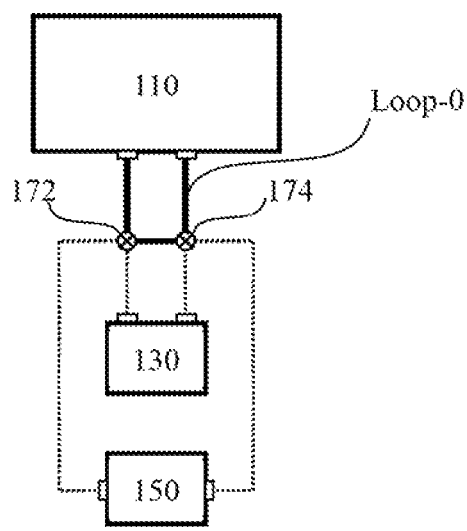
FIGS. 3A to 3D are views showing loops formed in respective steps for preparing a reference solution using the apparatus shown in FIG. 1.
Figure 3B:
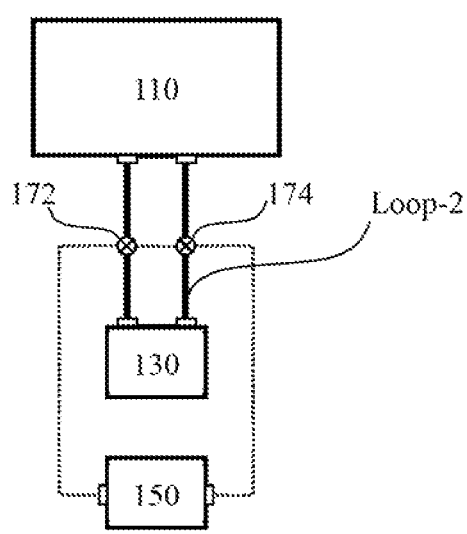
Figure 3C:
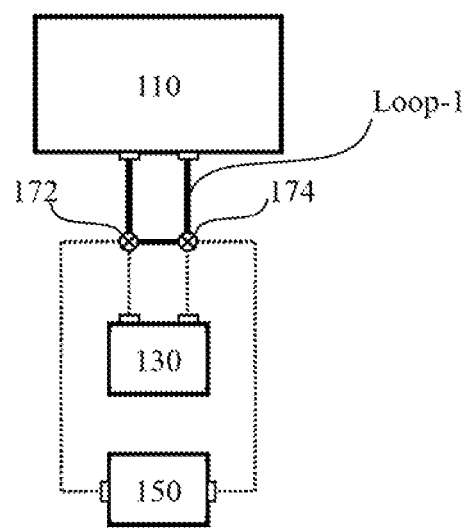
Figure 3D:
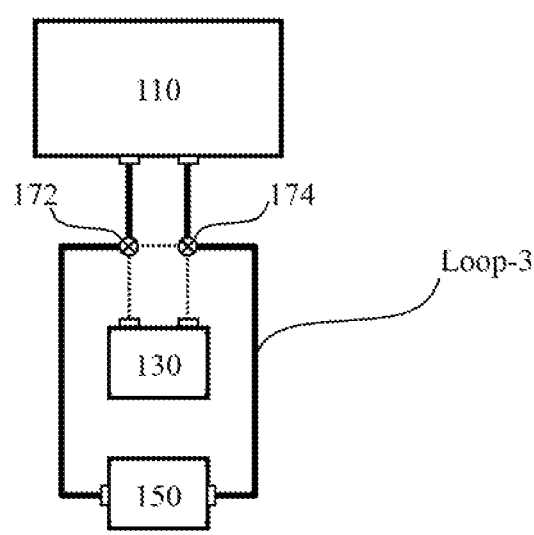

That is, by controlling the valves 172 and 174, the loop Loop-0 or Loop-1 (i.e., a closed loop connecting reference numerals 110, 172, 174 and 110 in the embodiment) is formed so that the gas component detector 110 is not connected to both the gas vessel 130 and the reference solution preparation vessel 150 as shown by a bold line in FIG. 3A or 3C, the loop Loop-2 (i.e., a closed loop connecting reference numerals 110, 172, 130, 174 and 110 in the embodiment) is formed so that the gas component detector 110 is connected to the gas vessel 130 and not connected to the reference solution preparation vessel 150 as shown by a bold line in FIG. 3B, and the loop Loop-3 (i.e., a closed loop connecting reference numerals 110, 172, 150, 174 and 110 in the embodiment) is formed so that the gas component detector 110 is connected to the reference solution preparation vessel 150 and not connected to the gas vessel 130 as shown by a bold line in FIG. 3D.

Here, the internal volumes of the loops Loop-1 and Loop-3 among the loops are used in the measurement of the radon concentration in the prepared radon reference solution. It should be noted that the internal volumes of the loops Loop-1 and Loop-3 include the volume of the internal path of the gas component detector 110 from the input port 112 to the output port 114 thereof, the volume of the internal space of the reference solution preparation vessel 150 and/or the volume of the internal spaces of the valves 172 and 174 in addition to the internal volume of the corresponding pipe lines PL. As the internal volume of each loop, only a macroscopic space in the loop is basically taken into consideration. Therefore, in the case of the reference solution preparation vessel 150, a volume obtained by subtracting the volume occupied by the solvent from the entire internal volume of the reference solution preparation vessel 150 is included in the internal volume of the corresponding loop.

Next, a method of preparing a radon reference solution using the preparation apparatus 100 so configured will be described with reference to FIGS. 2 and 3A to 3D.

First, radon gas and a liquid substance for preparing a reference solution are accommodated in the gas vessel 130 and the reference solution preparation vessel 150, respectively (S110). Here, the preparation apparatus 100 should be in the state of the loop Loop-0, in which the input and output ports 112 and 114 of the gas component detector 110 are directly connected to each other through the pipe line PL as shown in FIG. 3A by operating the valves 172 and 174 in order for the gas component detector 110 not to be connected to the gas vessel 130 and the reference solution preparation vessel 150. Here, if an opening/closing valve is installed at each of the ports 132 and 134 of the gas vessel 130 and is in a closed state, the preparation apparatus 100 may be in a state of any loop.

Then, the gas component detector 110 is operated in the state of the loop Loop-0 as shown in FIG. 3A. Here, the air of a measuring room occurs in the loop Loop-0 so configured. While the air circulates in the loop Loop-0 by means of the pump provided in the gas component detector 110 in the operation thereof, the component detection part of the gas component detector 110 measures the background concentration $C_0$ of the radon gas that essentially occurs in the air in the loop Loop-0 (S120). That is, the background concentration $C_0$ of radon gas refers to the concentration of the radon gas that essentially occurs in the measuring room, specifically in the preparation apparatus 100 and the pipe lines PL. The concentration of radon gas in the loop Loop-1 or Loop-3 formed later can be more precisely obtained by subtracting the background concentration $C_0$ from the radon concentration measured in each loop. However, if the background concentration of radon gas can be obtained from the information about the measuring room, the step of measuring the background concentration $C_0$ may be omitted.

Meantime, the order of the step S110 of respectively accommodating the radon gas and the liquid substance in the gas vessel 130 and the reference solution preparation vessel 150 and the step S120 of measuring the background concentration $C_0$ of radon gas may be changed.

Thereafter, the loop Loop-2, in which the gas component detector 110 and the gas vessel 130 are connected to each other as shown in FIG. 3B, is formed by operating the valves 172 and 174, thereby allowing the radon gas concentrated in the gas vessel 130 to enter the loop Loop-2 (S130). Here, if the ports 132 and 134 of the gas vessel 130 are respectively provided with opening/closing valves, these valves should be in an open state. By maintaining the loop Loop-2 for about 10 minutes, the radon gas is allowed to uniformly occur in the loop Loop-2. Here, it is possible to allow the radon gas to circulate in the loop Loop-2 and rapidly reach the uniform state by operating the pump of the gas component detector 110.

Then, the loop Loop-1, in which the input and output ports 112 and 114 of the gas component detector 110 are connected through the pipe line PL so that the valves 172 and 174 are directly connected to each other as shown in FIG. 3C, is formed by operating the valves 172 and 174. After maintaining the loop Loop-1 for a predetermined time, the component detection part of the gas component detector 110 measures the radon gas concentration $C_1$ in the loop Loop-1 (S140). Here, it is preferred that the radon gas concentration $C_1$ measured in the loop Loop-1 be corrected by subtracting the background concentration $C_0$ of radon gas measured in the step S120 therefrom. In practice, since the loops Loop-0 and Loop-1 have the same route but contain the substances having different concentrations, the loops Loop-0 and Loop-1 are expressed differentially from each other.

Thereafter, the loop Loop-3, in which the gas component detector 110 and the reference solution preparation vessel 150 are connected to each other as shown in FIG. 3D, is formed by operating the valves 172 and 174. Then, if the radon gas reaches an equilibrium state in the loop Loop-3, a radon reference solution is prepared in the reference solution preparation vessel 150. Here, the radon gas concentration $C_3$ in the loop Loop-3 is measured (S150). If the loop Loop-3 is formed as shown in FIG. 3D, the radon gas that has existed in the loop Loop-1 is introduced into the reference solution preparation vessel 150 through the loop Loop-3, and the introduced radon gas is partially dissolved in the liquid substance in the reference solution preparation vessel 150, whereby a radon reference solution is prepared. Here, the measured radon gas concentration $C_1$ is a value measured after the dissolution is completed and the equilibrium state is reached. It is also preferred that the radon gas concentration $C_3$ measured in the loop Loop-3 be corrected by subtracting the background concentration $C_0$ of radon gas measured in the step S120 therefrom.

If the radon reference solution is prepared as described above, the concentration $C_L$ of radon gas dissolved in the prepared radon reference solution is calculated according to the following procedure using the radon gas concentrations $C_1$, and $C_3$ in the loops Loop-1 and Loop-3 (S160).

A mass balance equation for radon gas in the loops Loop-1 and Loop-3 is as follows:

$$C_1 * V_1 = C_3 * V_3 + C_L * V_L \qquad \text{(Equation 1)}$$

wherein $C_1$ and $C_3$ are respectively the radon gas concentrations in the loops Loop-1 and Loop-3, $V_1$ and $V_3$ are respectively the internal volumes of the loops Loop-1 and Loop-3, and $V_L$ is the volume of the liquid substance or the prepared radon reference solution accommodated in the reference solution preparation vessel 150. As described above, $C_1$ and $C_3$ are respectively measured in steps S140 and S150, and $V_1$, $V_3$ and $V_L$ may be obtained from the volume of the internal path of the gas component detector 110, the internal volume of the reference solution preparation vessel 150, the volume of the solution accommodated therein, and the internal volume of the pipe lines PL, which will be described later again.

If Equation 1 is rearranged to solve for $C_L$, the concentration of radon gas dissolved in radon reference solution is calculated as follows:

$$C_L = (C_1 * V_1 - C_3 * V_3) / V_L \qquad \text{(Equation 2)}$$

In the meantime, $V_1$ and $V_3$ may be calculated as follows.

First, the internal volume $V_1$ of the loop Loop-1, which connects reference numerals 110, 172, 174 and 110, is the sum of the volume of the internal path of the gas component detector 110 from the input port 112 to the output port 114 thereof, the internal volume of the pipe lines PL from the input port 112 of the gas component detector 110 to the output port 114 of the gas component detector 110 via the valves 172 and 174, and the volume of the internal path of the valves 172 and 174. The volume of the internal path of each of the gas component detector 110 and the valves 172 and 174 may be obtained from its specification, and the internal volume of the pipe line PL may be obtained using its inner diameter and length or from a conventional method such as a weight method.

The weight method is used to obtain the internal volume of the pipe line PL by filling the pipe line PL with a fluid, the density of which is known, such as distilled water, and then obtaining the internal volume of the pipe line PL from the mass of the distilled water.

The internal volume $V_3$ of the loop Loop-3, which connects reference numerals 110, 172, 150, 174 and 110, is the sum of the volume of the internal path of the gas component detector 110 from the input port 112 to the output port 114 thereof, the internal volume of the pipe lines PL from the input port 112 of the gas component detector 110 to the output port 114 of the gas component detector 110 via the valve 172, the reference solution preparation vessel 150 and the valve 174, the volume obtained by subtracting the volume $V_L$ of the solvent from the total internal volume of the reference solution preparation vessel 150, and the volume of the internal path of the valves 172 and 174. The volume of the internal path of the gas component detector 110, the internal volume of the pipe lines PL and the volume of the internal path of the valves 172 and 174 each may be obtained in the same manner as described above, the internal volume of the reference solution preparation vessel 150 may be obtained from the specification thereof or the weight method.

The internal volume of each component may be obtained using various methods other than the aforementioned methods. For example, the internal path volume of the gas component detector 110 may be obtained using the apparatus of the present invention as follows.

Using the aforementioned apparatus 100, some (S120 to S150) of the steps of the aforementioned reference solution preparing method is preformed in a state where the reference solution preparation vessel 150 is filled with no liquid substance, i.e., in a state of the empty vessel. That is, a gaseous substance that can be measured in the gas component detector 110 is accommodated in the gas vessel 130, the background concentration $C_0$ of the gaseous substance is measured in the loop Loop-0 shown in FIG. 3A (corresponding to S120); the loop Loop-2 is formed as shown in FIG. 3B and then the gaseous substance is uniformly distributed in the loop Loop-2 (corresponding to S130); the loop Loop-1 is formed as shown in FIG. 3C and the concentration $C_1$ of the gaseous substance is measured therein (corresponding to S140); and the loop Loop-3 is formed as shown in FIG. 3D and maintained for a predetermined time and the concentration $C_3$ of the gaseous substance is measured in the loop Loop-3 (corresponding to S150). Thereafter, the internal path volume of the gas component detector 110 may be calculated according to the following procedure.

A mass balance equation for the gaseous substance in the loops Loop-1 and Loop-3 is as follows:

$$C_1 * V_1 = C_3 * V_3 \quad \text{(Equation 3)}$$

The internal volumes $V_1$ and $V_3$ of the loops Loop-1 and Loop-3 each may be specifically subdivided as follows.

The internal volume $V_1$ of the loop Loop-1 is the sum of the internal path volume $V_d$ of the gas component detector 110, the internal volume $V_{P1}$ of the pipe lines PL constituting the loop Loop-1, and the volume $V_V$ of the internal path of both the valves 172 and 174. That is, $V_1 = V_d + V_{P1} + V_V$.

The internal volume $V_3$ of the loop Loop-3 is the sum of the internal path volume $V_d$ of the gas component detector 110, the internal volume $V_{P3}$ of the pipe lines PL constituting the loop Loop-3, the internal volume $V_E$ of the empty vessel 150, and the volume $V_V$ of the internal path of both the valves 172 and 174. That is, $V_3 = V_d + V_{P3} + V_E + V_V$.

The following Equation 4 is obtained by substituting $V_1$ and $V_3$ into Equation 3.

$$C_1 * (V_d + V_{P1} + V_V) = C_3 * (V_d + V_{P3} + V_E + V_V) \quad \text{(Equation 4)}$$

If Equation 4 is rearranged to solve for the internal path volume $V_d$ of the gas component detector 110, the internal path volume $V_d$ is obtained as follows:

$$V_d = (C_3 * (V_{P3} + V_E) - C_1 * V_{P1} + (C_3 - C_1) * V_V)/(C_1 - C_3) \quad \text{(Equation 5)}$$

Meanwhile, in the above-described embodiment, although the gas component detector 110 and the valves 172 and 174 may be individually operated by an operator, an additional controller may be provided to automatically perform the above-described preparation/measurement steps after the radon gas and the liquid substance for preparing a reference solution are respectively accommodated in the gas vessel 130 and the reference solution preparation vessel 150.

It is preferred that not only the temperature and pressure but also the concentration measuring time be reported when the radon reference solution is prepared according to the above-described embodiment and its concentration is measured, and then, the temperature and pressure conditions of the concentration of the prepared radon reference solution and the concentration measuring time be specified together.

The radon concentration of the prepared reference solution is rapidly reduced according to the following radioactive decay equation as time passes since radon has short half-life.

$$C_{Lt} = C_{L0} * e^{(-\lambda t)} \quad \text{(Equation 6)}$$

wherein $C_{Lt}$ is the radon concentration when the radon reference solution is used, $C_{L0}$ is the radon concentration when the radon reference solution is prepared (i.e., $C_L$ in Equation 2), $\lambda$ is the decay constant of radon, which is 0.00756 h$^{-1}$, t is a time period (hour) from the time when the radon concentration of the radon reference solution is measured to the time when the radon reference solution is used.

In addition, an air-liquid partition coefficient ($K_{L/A} = C_L / C_A$, wherein $C_A$ is the concentration of radon in the space of the reference solution preparation vessel 150 except the radon reference solution) of the prepared radon reference solution in the reference solution preparation vessel 150, i.e., a distribution ratio of radon in the solution to radon in the air, varies depending on temperature, which is expressed as the following well-known equation:

$$K_{L/A} = 0.105 + 0.405 * \exp(-0.052T) \quad \text{(Equation 7)}$$

wherein T (° C.) is the temperature of the solvent when the reference solution is used, and the used solvent is water.

That is, when the radon reference solution is used, the radon concentration of the reference solution should be corrected using Equations 6 and 7 by confirming the elapsed time t from the time when the radon concentration is measured in the preparing the radon reference solution and the temperature T of the radon reference solution when it is used.

Since according to the present invention, a liquid substance of a target object to be measured is placed into the reference solution preparation vessel 150 and the radon reference solution is prepared, the prepared radon reference solution and the liquid substance of the target object to be measured have the same component, thereby securing a matrix matching condition in calibrating a measuring device. However, if the component of the radon reference solution is different from that of the liquid substance of the target object to be measured, the partition coefficient may also be different and thus should be corrected.

Figure 4:
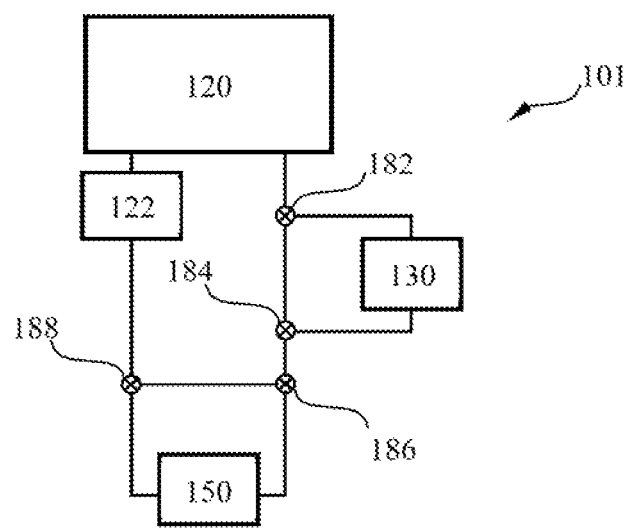
FIG. 4 is a schematic view of an apparatus of preparing a reference solution according to a modified embodiment of the present invention.

Next, an apparatus of preparing a reference solution according to a modified embodiment of the present invention will be described. FIG. 4 is a schematic view of an apparatus of preparing a reference solution according to a modified embodiment of the present invention; and FIGS. 5A to 5D are views showing loops formed in respective steps for preparing a reference solution using the apparatus shown in FIG. 4.

In the modified embodiment, the same reference numerals are used for the same elements as those of the previous embodiment, and repeated descriptions will be omitted.

Referring to FIG. 4, a reference solution preparation apparatus 101 according to the modified embodiment of the present invention includes a gas component detector 120 for measuring the concentration of radon gas, a pump 122, a gas vessel 130 for accommodating radon-enriched gas, a reference solution preparation vessel 150 for accommodating a liquid substance of a target object desirous to be measured, pipe lines PL for connecting the above-described components, and a plurality of valves 182, 184, 186 and 188 installed at predetermined positions of the pipe lines PL to switch between a plurality of predetermined loops formed by the gas component detector 120, the pump 122, the gas vessel 130, the reference solution preparation vessel 150, and the pipe lines PL.

The gas component detector 120 is the same as the gas component detector 110 of the previous embodiment except that the gas component detector 120 does not have a pump housed therein. The gas component detector 120 corresponds to the component detection part of the gas component detector 110 of the previous embodiment, and the pump 122 corresponds to the pump of the gas component detector 110. That is, the gas component detector 120 and the pump 122 of the modified embodiment, into which the component detection part and the pump housed in the gas component detector 110 of the previous embodiment are separated, are substantially the same as the gas component detector 110. In the apparatus of preparing a reference solution according to the present invention, since the pump serves to assist radon gas in the formed loop in being uniform in the loop, the pump is a substantially optional element. Therefore, the pump 122 may be omitted in the modified embodiment, and the gas component detector 110 may also have no pump housed therein in the previous embodiment.

The gas vessel 130 and the reference solution preparation vessel 150 are respectively the same as the gas vessel 130 and the reference solution preparation vessel 150 of the previous embodiment.

The gas component detector 120, the pump 122, the gas vessel 130 and the reference solution preparation vessel 150 are connected to one another through the pipe lines PL so that they serially form one closed loop. In addition, there are further provided paths, which do not pass through the gas vessel 130 and the reference solution preparation vessel 150 but bypath them, respectively. That is, the valves 182 and 184 are respectively installed at the pipe lines PL in the vicinity of the two ports of the gas vessel 130 and connected to each other through a pipe line PL, and the valves 186 and 188 are respectively installed at the pipe lines PL in the vicinity of the two ports of the reference solution preparation vessel 150 and connected to each other through a pipe line PL.

By controlling the valves 182, 184, 186 and 188 in the state that the pipe lines PL and the valves 182, 184, 186 and 188 are connected to one another and installed as described above, loops Loop-0, Loop-1, Loop-2 and Loop-3 each having the same path as those of the previous embodiment may be formed.

Figure 5A:
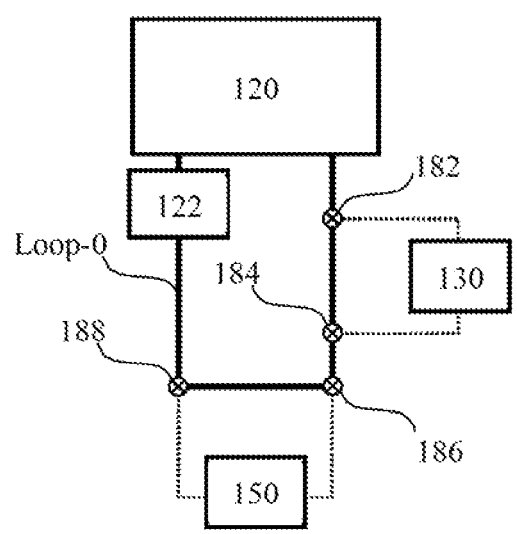
FIGS. 5A to 5D are views showing loops formed in respective steps for preparing a reference solution using the apparatus shown in FIG. 4.
Figure 5B:
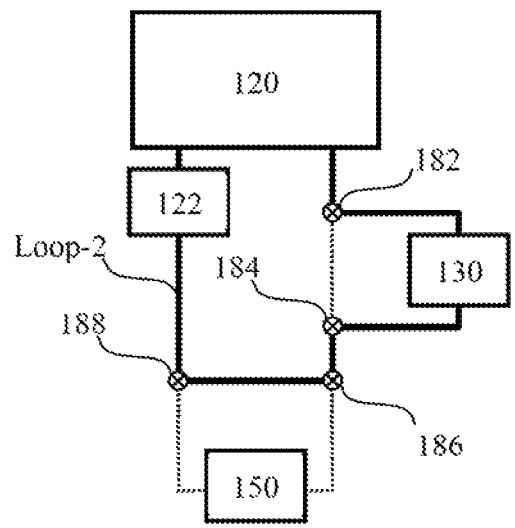
Figure 5C:
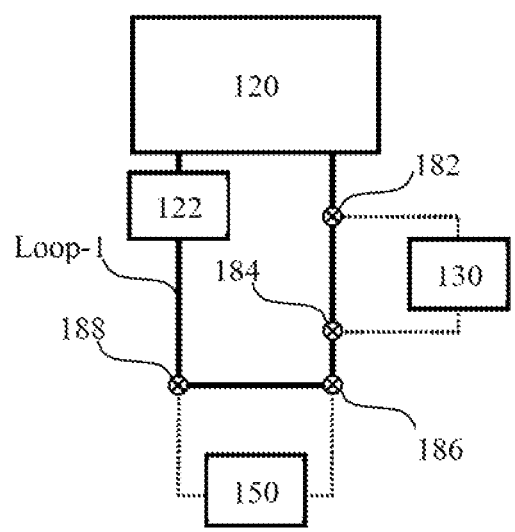
Figure 5D:
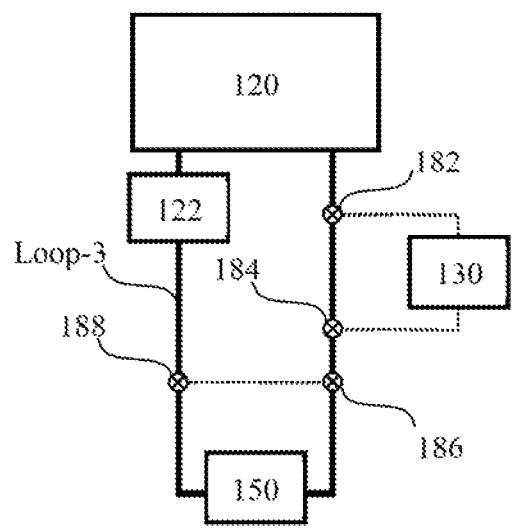

That is, by controlling the valves 182, 184, 186 and 188, the loop Loop-0 or Loop-1 (i.e., a closed loop connecting reference numerals 120, 182, 184, 186, 188, 122 and 120 in the modified embodiment) is formed so that the gas component detector 120 is not connected to both the gas vessel 130 and the reference solution preparation vessel 150 as shown by a bold line in FIG. 5A or 5C, the loop Loop-2 (i.e., a closed loop connecting reference numerals 120, 182, 130, 184, 186, 188, 122 and 120 in the modified embodiment) is formed so that the gas component detector 120 is connected to the gas vessel 130 and not connected to the reference solution preparation vessel 150 as shown by a bold line in FIG. 5B, and the loop Loop-3 (i.e., a closed loop connecting reference numerals 120, 182, 184, 186, 150, 188, 122 and 120 in the modified embodiment) is formed so that the gas component detector 120 is connected to the reference solution preparation vessel 150 and not connected to the gas vessel 130 as shown by a bold line in FIG. 5D.

In the modified embodiment, the connection configuration of the pipe lines and the valves is somewhat changed and the number of the valves is increased, as compare with the previous embodiment. The valves used in the modified embodiment are increased in number and are not four-way valves but three-way valves.

Substantially, if the valves 182 and 188 are combined and substituted by one four-way valve and the valves 184 and 186 are combined and substituted by one four-way valve, the modified embodiment has the same configuration as the previous embodiment.

A method of preparing a radon reference solution using the preparation apparatus 101 so configured is the same as the method described in the previous embodiment.

That is, radon gas and a liquid substance for preparing a reference solution are respectively accommodated in the gas vessel 130 and the reference solution preparation vessel 150 (S110); the background concentration $C_0$ of radon gas is measured in the loop Loop-0 shown in FIG. 5A (S120); the loop Loop-2 is formed as shown in FIG. 5B and the radon gas is uniformly distributed in the loop Loop-2 (S130); the loop Loop-1 is formed as shown in FIG. 5C and the radon gas concentration $C_1$ is measured therein (S140); and the loop Loop-3 is formed as shown in FIG. 5D, the radon gas is allowed to reach an equilibrium state therein to prepare a radon reference solution and the radon gas concentration $C_3$ is measured in the loop Loop-3 (S150). If the radon reference solution is prepared and the radon gas concentrations $C_1$ and $C_3$ are measured as described above, the concentration of the radon gas dissolved in the radon reference solution is calculated using the above-described Equation 2 (S160).

In this modified embodiment, although the gas component detector 120, the pump 122, and the valves 182, 184, 186 and 188 may be individually operated by an operator, an additional controller may be provided to automatically perform the above-described preparation/measurement steps after the radon gas and the liquid substance for preparing a reference solution are respectively accommodated in the gas vessel 130 and the reference solution preparation vessel 150.

Meanwhile, if the respective components, i.e., the gas component detector 110 or 120, the gas vessel 130, the reference solution preparation vessel 150, the pipe lines PL and the valves are connected to one another to form the loops Loop-0, Loop-1, Loop-2 and Loop-3, they may be changed in positions, order and/or number to be modified into any other forms. However, when the pump 122 is included, it is preferred that the pump 122 be installed adjacent to the gas component detector 120.

In addition, a drying tube may be further installed adjacent to the gas component detector 110 or 120. A desiccant is provided in the drying tube to remove moisture from the gaseous substance passing through the drying tube. In the state that the loop Loop-1 is formed in the apparatus of preparing a reference solution 100 or 101 according to the present invention, while the air circulating in the loop Loop-1 passes through the drying tube, the moisture inside the loop Loop-1, particularly the gas component detector 110 or 120 is removed, whereby it is possible to more precisely measure the concentration of radon.

An apparatus and method of preparing a reference solution according to the present invention so configured is simple in constitution, and thus, it is possible to simply and precisely prepare a reference solution of a gaseous substance of a target object desirous to be measured using a liquid substance of the target object as a solvent.

In particular, when a radon reference solution is prepared, although it is difficult to secure long-term stability because of a short half-life of radon, such long-term stability can be somewhat secured since the reference solution can be easily prepared in-situ.

Further, since a reference solution of a gaseous substance of a target object desirous to be measured is prepared using a liquid substance of the target object as a solvent, there is an advantage in that a matrix matching condition can be secured.

Although some embodiments of the present invention are described for illustrative purposes, it will be apparent to those skilled in the art that various modifications and changes can be made thereto within the scope of the invention without departing from the essential features of the invention. Accordingly, the aforementioned embodiments should be construed not to limit the technical spirit of the present invention but to be provided for illustrative purposes so that those skilled in the art can fully understand the spirit of the present invention. The scope of the present invention should not be limited to the aforementioned embodiments but defined by appended claims. The technical spirit within the scope substantially identical with the scope of the present invention will be considered to fall in the scope of the present invention defined by the appended claims.

What is claimed is:

1. An apparatus for preparing a reference solution, comprising:
    a gas component detector having two ports and configured to measure a concentration of a predetermined gaseous substance;
    a gas vessel having two ports and configured to accommodate the predetermined gaseous substance;
    a reference solution preparation vessel having two ports and configured to accommodate a predetermined liquid substance;
    pipe lines connecting the ports of the gas component detector, the gas vessel and the reference solution preparation vessel; and
    valves installed on the pipe lines,
    wherein the pipe lines and the valves are arranged and installed to form a first loop wherein the gas component detector is not connected to both the gas vessel and the reference solution preparation vessel, a second loop wherein the gas component detector is connected to the gas vessel and not connected to the reference solution preparation vessel, and a third loop wherein the gas component detector is connected to the reference solution preparation vessel and not connected to the gas vessel, and the valves switches between the loops.

2. The apparatus according to claim 1, wherein the two ports of the gas component detector are respectively connected to the two ports of the gas vessel through two pipe lines, the valves are respectively installed on the two pipe lines, the valves are connected to each other through a pipe line, the valves are respectively connected to the two ports of the reference solution preparation vessel through two pipe lines, and each of the valves is a four-way valve.

3. The apparatus according to claim 2, further comprising a pump installed adjacent to the gas component detector.

4. The apparatus according to claim 2, further comprising a drying tube installed adjacent to the gas component detector.

5. The apparatus according to claim 2, wherein each port of the gas vessel is provided with an opening/closing valve.

6. The apparatus according to claim 2, wherein the reference solution preparation vessel is configured to be removable from the apparatus and comprises a dual cap including a septum cap.

7. The apparatus according to claim 1, wherein the gas component detector, the gas vessel, and the reference solution preparation vessel are serially connected to one another through pipe lines to form a single closed loop, the valves are respectively installed at the pipe lines in the vicinity of the two ports of the gas vessel and connected to each other through a pipe line, the valves are respectively installed at the pipe lines in the vicinity of the two ports of the reference solution preparation vessel and connected to each other through a pipe line, and each of the valves is a three-way valve.

8. The apparatus according to claim 7, further comprising a pump installed adjacent to the gas component detector.

9. The apparatus according to claim 7, further comprising a drying tube installed adjacent to the gas component detector.

10. The apparatus according to claim 7, wherein each port of the gas vessel is provided with an opening/closing valve.

11. The apparatus according to claim 7, wherein the reference solution preparation vessel is configured to be removable from the apparatus and comprises a dual cap including a septum cap.

12. The apparatus according to claim 1, further comprising a pump installed adjacent to the gas component detector.

13. The apparatus according to claim 1, further comprising a drying tube installed adjacent to the gas component detector.

14. The apparatus according to claim 1, wherein each port of the gas vessel is provided with an opening/closing valve.

15. The apparatus according to claim 1, wherein the reference solution preparation vessel is configured to be removable from the apparatus and comprises a dual cap including a septum cap.

16. A method of preparing a reference solution, comprising:
    ng the apparatus for preparing a reference solution according to claim 1;
    accommodating the predetermined gaseous substance and the predetermined liquid substance in the gas vessel and the reference solution preparation vessel, respectively;
    forming the second loop and maintaining it for a predetermined time;
    forming the first loop, maintaining it for a predetermined time, and measuring a concentration of the gaseous substance in the first loop by the gas component detector;
    forming the third loop, maintaining it for a predetermined time for the gaseous substance and the liquid substance to reach an equilibrium state in the reference solution preparation vessel, thereby obtaining a reference solution of the gaseous substance, and measuring a concentration of the gaseous substance in the third loop by the gas component detector; and
    calculating a gaseous substance concentration in the reference solution based on the respective gaseous substance concentrations in the first and third loops, respective internal volumes of these loops, a volume of the liquid substance, and a mass balance equation for the gaseous substance in these loops.

17. The method according to claim 16, before the second loop is formed, the method further comprising additionally forming the first loop to measure a background concentration of the gaseous substance in the additional first loop by the gas component detector, wherein after forming the second loop, the gaseous substance concentrations measured in the first and third loops by the gas component detector are corrected by subtracting the background concentration therefrom.

18. The method according to claim 16, wherein a solid substance generating the gaseous substance is accommodated in the gas vessel.

19. The method according to claim 16, wherein the gaseous substance comprises radon or a volatile substance.

* * * * *